United States Patent
Dale et al.

(10) Patent No.: US 9,724,695 B2
(45) Date of Patent: Aug. 8, 2017

(54) SYSTEMS AND METHODS FOR AMPLIFYING NUCLEIC ACIDS

(75) Inventors: Gregory A. Dale, Gaithersburg, MD (US); Kenton C. Hasson, Gaithersburg, MD (US); Shulin Zeng, Gaithersburg, MD (US); Michele Stone, Rockville, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 0 days.

(21) Appl. No.: 12/144,328

(22) Filed: Jun. 23, 2008

(65) Prior Publication Data

US 2009/0317874 A1 Dec. 24, 2009

(51) Int. Cl.
*B01L 1/00* (2006.01)
*B01L 3/00* (2006.01)
(Continued)

(52) U.S. Cl.
CPC .............. *B01L 7/525* (2013.01); *B01L 3/5027* (2013.01); *B01L 2300/0654* (2013.01);
(Continued)

(58) Field of Classification Search
CPC .... B01L 3/5027; B01L 3/502715; B01L 7/00; B01L 7/52
See application file for complete search history.

(56) References Cited

U.S. PATENT DOCUMENTS 6,018,616 A 1/2000 Schaper
6,020,187 A 2/2000 Tam
(Continued)

FOREIGN PATENT DOCUMENTS

WO 98/33403 A1 8/1998
WO 2005075683 A1 8/2005

OTHER PUBLICATIONS

Lagally et al., "Single-Molecule DNA Amplification and Analysis in an Integrated Microfluidic Device," Analytical Chemistry, vol. 73, No. 3, (2001) pp. 565-570.
(Continued)

*Primary Examiner* — Nathan Bowers
(74) *Attorney, Agent, or Firm* — Rothwell, Figg, Ernst & Manbeck, P.C.

(57) ABSTRACT

An apparatus for performing a thermocyclic process, such as amplifying DNA, includes a microfluidic chip with a channel formed therein and one or more thermal distribution elements disposed over portions of the chip. Each thermal distribution element is configured to distribute thermal energy from an external thermal energy source substantially uniformly over the portion of the chip covered by the thermal distribution element. The portion of the chip covered by the thermal distribution element thereby comprises a discrete temperature zone. Other temperature zones can be defined by other thermal distribution elements or by portions of the chip not covered by a thermal distribution element. The channel is configured so that a fluid flowing through the channel would enter and exit the different temperature zones a plurality of times, thereby alternately exposing the fluid to the temperature of each zone for a period of time required for the fluid to traverse the zone.

32 Claims, 8 Drawing Sheets

(51) Int. Cl.
    *B01L 7/00*     (2006.01)
    *G01N 21/03*     (2006.01)
    *G01N 21/05*     (2006.01)
    *G01N 21/64*     (2006.01)

(52) U.S. Cl.
CPC ......... *B01L 2300/0816* (2013.01); *B01L 2300/0861* (2013.01); *B01L 2300/0883* (2013.01); *B01L 2300/1822* (2013.01); *B01L 2300/1827* (2013.01); *B01L 2300/1838* (2013.01); *B01L 2400/0487* (2013.01); *G01N 21/0332* (2013.01); *G01N 2021/0346* (2013.01); *G01N 2021/058* (2013.01); *G01N 2021/6439* (2013.01)

(56) References Cited

U.S. PATENT DOCUMENTS

| | | | |
|---|---|---|---|
| 6,541,274 B2 | 4/2003 | Nagle et al. | |
| 6,680,193 B1* | 1/2004 | Fouillet et al. | 435/287.2 |
| 6,896,855 B1 | 5/2005 | Kohler et al. | |
| 6,960,437 B2 | 11/2005 | Enzelberger et al. | |
| 6,964,862 B2* | 11/2005 | Chen | 435/91.2 |
| 7,156,969 B2* | 1/2007 | Mehta et al. | 204/455 |
| 7,498,164 B2* | 3/2009 | Oldham et al. | 435/288.7 |
| 2001/0036634 A1* | 11/2001 | Chow et al. | 435/6 |
| 2002/0191826 A1* | 12/2002 | Benett et al. | 382/129 |
| 2005/0042639 A1 | 2/2005 | Knapp et al. | |
| 2005/0129582 A1 | 6/2005 | Breidford et al. | |
| 2007/0190641 A1* | 8/2007 | Wilding et al. | 435/288.5 |
| 2008/0176289 A1* | 7/2008 | Zeng et al. | 435/91.2 |
| 2008/0280285 A1* | 11/2008 | Chen et al. | 435/5 |
| 2008/0280331 A1* | 11/2008 | Davies et al. | 435/91.2 |

OTHER PUBLICATIONS

Kopp et al., "Chemical Amplification: Continuous-Flow PCR on a Chip," Science, vol. 280, (1998) pp. 1046-1048.

Park et al., "Cylindrical compact thermal-cycling device for continuous-flow polymerase chain reaction," Analytical Chemistry, vol. 75 (2003) pp. 6029-6033.

* cited by examiner

SYSTEMS AND METHODS FOR AMPLIFYING NUCLEIC ACIDS

BACKGROUND

Field of the Invention

The present invention relates to systems and methods for amplifying nucleic acids. In some embodiments, the present invention relates to systems and methods for performing a real-time polymerase chain reaction (PCR) in continuous-flow microfluidic systems and to methods for monitoring real-time PCR in such systems.

Discussion of the Background

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, may facilitate disease diagnosis and prognosis, marker assisted selection, correct identification of crime scene features, the ability to propagate industrial organisms and many other techniques. Determination of the integrity of a nucleic acid of interest can be relevant to the pathology of an infection or cancer.

One of the most powerful and basic technologies to detect small quantities of nucleic acids is to replicate some or all of a nucleic acid sequence many times, and then analyze the amplification products. PCR is perhaps the most well-known of a number of different amplification techniques.

PCR is a powerful technique for amplifying short sections of DNA. With PCR, one can quickly produce millions of copies of DNA starting from a single template DNA molecule. PCR includes a three phase temperature cycle of denaturation of DNA into single strands, annealing of primers to the denatured strands, and extension of the primers by a thermostable DNA polymerase enzyme. This cycle is repeated so that there are enough copies to be detected and analyzed.

In principle, each cycle of PCR could double the number of copies. In practice, the multiplication achieved after each cycle is always less than 2. Furthermore, as PCR cycling continues, the buildup of amplified DNA products eventually ceases as the concentrations of required reactants diminish.

For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005), and *PCR Protocols A Guide to Methods and Applications*, M. A. Innis et al., eds., Academic Press Inc. San Diego, Calif. (1990).

Real-time PCR refers to a growing set of techniques in which one measures the buildup of amplified DNA products as the reaction progresses, typically once per PCR cycle. Monitoring the accumulation of products over time allows one to determine the efficiency of the reaction, as well as to estimate the initial concentration of DNA template molecules. For general details concerning real-time PCR see *Real-Time PCR: An Essential Guide*, K. Edwards et al., eds., Horizon Bioscience, Norwich, U.K. (2004).

Several different real-time detection chemistries now exist to indicate the presence of amplified DNA. Most of these depend upon fluorescence indicators that change properties as a result of the PCR process. Among these detection chemistries are DNA binding dyes (such as SYBR® Green) that increase fluorescence efficiency upon binding to double stranded DNA. Other real-time detection chemistries utilize Foerster resonance energy transfer (FRET), a phenomenon by which the fluorescence efficiency of a dye is strongly dependent on its proximity to another light absorbing moiety or quencher. These dyes and quenchers are typically attached to a DNA sequence-specific probe or primer. Among the FRET-based detection chemistries are hydrolysis probes and conformation probes. Hydrolysis probes (such as the TaqMan® probe) use the polymerase enzyme to cleave a reporter dye molecule from a quencher dye molecule attached to an oligonucleotide probe. Conformation probes (such as molecular beacons) utilize a dye attached to an oligonucleotide, whose fluorescence emission changes upon the conformational change of the oligonucleotide hybridizing to the target DNA.

A number of commercial instruments exist that perform real-time PCR. Examples of available instruments include the Applied Biosystems PRISM 7500, the Bio-Rad iCylcer, and the Roche Diagnostics LightCycler 2.0. The sample containers for these instruments are closed tubes which typically require at least a 10 µl volume of sample solution. If the lowest concentrations of template DNA detectable by a particular assay were on the order of one molecule per microliter, the detection limit for available instruments would be on the order of tens of targets per sample tube. Therefore, in order to achieve single molecule sensitivity, it is desirable to test smaller sample volumes, in the range of 1-1000 nl.

More recently, a number of high throughput approaches to performing PCR and other amplification reactions have been developed, e.g., involving amplification reactions in microfluidic devices, as well as methods for detecting and analyzing amplified nucleic acids in or on the devices. Thermal cycling of the sample for amplification is usually accomplished in one of two methods. In the first method, the sample solution is loaded into the device and the temperature is cycled in time, much like a conventional PCR instrument. In the second method, the sample solution is pumped continuously through spatially varying temperature zones.

For example, Lagally et al. (*Anal Chem* 73:565-570 (2001)) demonstrated amplification and detection of single template DNA in a 280 nl PCR chamber. Detection of products was made post-PCR using capillary electrophoresis. On the other hand, Kopp et al. (*Science* 280:1046-1048 (1998)) demonstrated continuous-flow PCR using a glass substrate with a serpentine channel passing over three constant temperature zones at 95° C. (denature), 72° C. (extension), and 60° C. (annealing). The 72° C. zone was located in the central region and had to be passed through briefly in going from 95° C. to 60° C. Detection was made post-PCR using gel electrophoresis. Since this PCR technique is not based on heating the entire surfaces of the reaction vessel, the reaction rate is determined by a flow rate, not a heating/cooling rate.

Park et al. (*Anal Chem* 75:6029-6033 (2003)) describe a continuous-flow PCR device that uses a polyimide coated fused silica capillary wrapped into a helix around three temperature-controlled blocks. Sample volumes were 2 µl. Detection was made post PCR using gel electrophoresis. Reference was made to the possibility of adapting their instrument for real-time PCR by using a capillary coated with PTFE instead of non-transparent polyimide. See also, Hahn et al. (WO 2005/075683).

Enzelberger et al. (U.S. Pat. No. 6,960,437) describe a microfluidic device that includes a rotary channel having three temperature zones. A number of integrated valves and pumps are used to introduce the sample and to pump it through the zones in a rotary fashion.

Knapp et al. (U.S. Patent Application Publication No. 2005/0042639) describe a microfluidic device capable of single molecule amplification. A planar glass device with several straight parallel channels is disclosed. A mixture of target DNA and PCR reagents is injected into these channels. In a first embodiment, the channels are filled with this mixture and flow is stopped. Then the entire length of the channels is thermally cycled. After thermal cycling is completed, the channels are imaged in order to detect regions of fluorescence where DNA has been amplified. In a second embodiment, the PCR mixture flows continuously through the amplification zone as the temperature is cycled, and fluorescence is detected downstream of the amplification zone. Different degrees of amplification are achieved by altering the time spent in cycling, through changing distance traveled under cycling, and the like. It is worth noting that this method varies conditions (such as cycles experienced) for separate consecutive sample elements, rather than monitoring the progress of individual sample elements over time.

US 2005/0129582A1, entitled System and method for heating, cooling and heat cycling on microfluidic device, describes an integrated heat exchange system on a microfluidic card. According to one aspect of the system, the portable microfluidic card has a heating, cooling, and heat cycling system on-board such that the card can be used portably. The microfluidic card includes one or more reservoirs containing exothermic or endothermic material.

Kohler et al. (U.S. Pat. No. 6,896,855) discusses a miniaturized temperature zone flow reactor that has fixed (non adjustable) temperature zones that can be used for thermocycling.

Various additional attempts have been made to develop an adequate device for monitoring and changing the temperature on a microfluidic device. For example, International Patent Application PCT/US98/1791 discusses devices that controls and monitors temperature within microfluidic systems by applying electric currents to fluids to generate heat therein, as well as measure solution conductivity as a measure of fluid temperature.

Another system for controlling temperature on a microfluidic device is described in U.S. Pat. No. 6,541,274. This patent is directed to a reactor system having a plurality of reservoirs in a substrate. A heat exchanger is inserted in the reservoirs to control the temperature. Still other examples of existing devices for controlling temperature on a microfluidic device is with radiant heat as described in U.S. Pat. No. 6,018,616, and the temperature regulated controlled block as described in U.S. Pat. No. 6,020,187.

SUMMARY

The present invention provides systems and methods for performing a thermocyclic process, such as amplifying nucleic acids.

Aspects of the invention are embodied in an apparatus for performing a thermocyclic process comprising a microfluidic chip having a fluid channel formed therein and one or more thermal distribution elements. The microfluidic chip is configured with two or more temperature zones. Each thermal distribution element is in thermal communication with an associated portion of the microfluidic chip, and each thermal distribution element is constructed and arranged to distribute thermal energy from an external thermal energy source substantially uniformly over the associated portion of the microfluidic chip, thereby defining the associated portion as one of the temperature zones within said microfluidic chip. The channel is arranged such that a fluid flowing through the channel would enter and exit each of the temperature zones of the microfluidic chip a plurality of times.

Still other aspects of the invention are embodied in a system for performing a thermocyclic process. The system comprises a microfluidic chip having a fluid channel formed therein, a thermal energy source, and detectors. The microfluidic chip is configured with two or more temperature zones and includes one or more thermal distribution elements in thermal communication with an associated portion of the microfluidic chip. Each thermal distribution element is constructed and arranged to distribute thermal energy from an external thermal energy source substantially uniformly over the associated portion of the microfluidic chip, thereby defining the associated portion as one of the temperature zones within the microfluidic chip. The channel is arranged such that a fluid flowing through the channel would enter and exit each of the temperature zones of the microfluidic chip a plurality of times.

A thermal energy source is associated with each thermal distribution element and is configured to apply thermal energy to the associated thermal distribution element. The detector is configured to detect emissions originating from one or more locations within the channel.

Still other aspects of the invention are embodied in a DNA amplification method. The method comprises providing an apparatus for amplifying DNA. The apparatus comprises a microfluidic chip having a channel, a first thermal distribution element, and a second thermal distribution element. The first thermal distribution element covers only a first portion of the microfluidic chip, and the second thermal distribution element covering only a second portion of the microfluidic chip that does not overlap with the first portion of the microfluidic chip. The first and second thermal distribution elements are arranged such that there is a gap between the first and second thermal distribution elements, the gap corresponding to a third portion of the microfluidic chip. The channel is configured such that a fluid flowing through the channel would enter and exit the first, second, and third portions of the microfluidic chip a plurality of times.

Thermal energy is applied to the first thermal distribution element to generate a first temperature in the first portion of the microfluidic chip, and thermal energy is applied to the second thermal distribution element to generate a second temperature in the second portion of the microfluidic chip. A third temperature may be generated in the third portion of the microfluidic chip. A solution containing a nucleic acid sample is pumped through the channel so that the solution alternately flows through the first, second, and third portions of the microfluidic chip and is alternately exposed to the first, second, and third temperatures.

The method further includes, while the solution is being pumped, detecting emissions originating from solution flowing through a portion of the channel disposed within the one of the portions of the microfluidic chip.

The above and other aspects and embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements.

DETAILED DESCRIPTION OF PREFERRED EMBODIMENTS

As used herein, the words "a" and "an" mean "one or more." Furthermore, unless defined otherwise, all technical and scientific terms used herein have the same meaning as commonly understood by one of ordinary skill in the art to which the invention pertains. Although any methods and materials similar or equivalent to those described herein can be used in the practice of the present invention, the preferred materials and methods are described herein.

Figure 1:
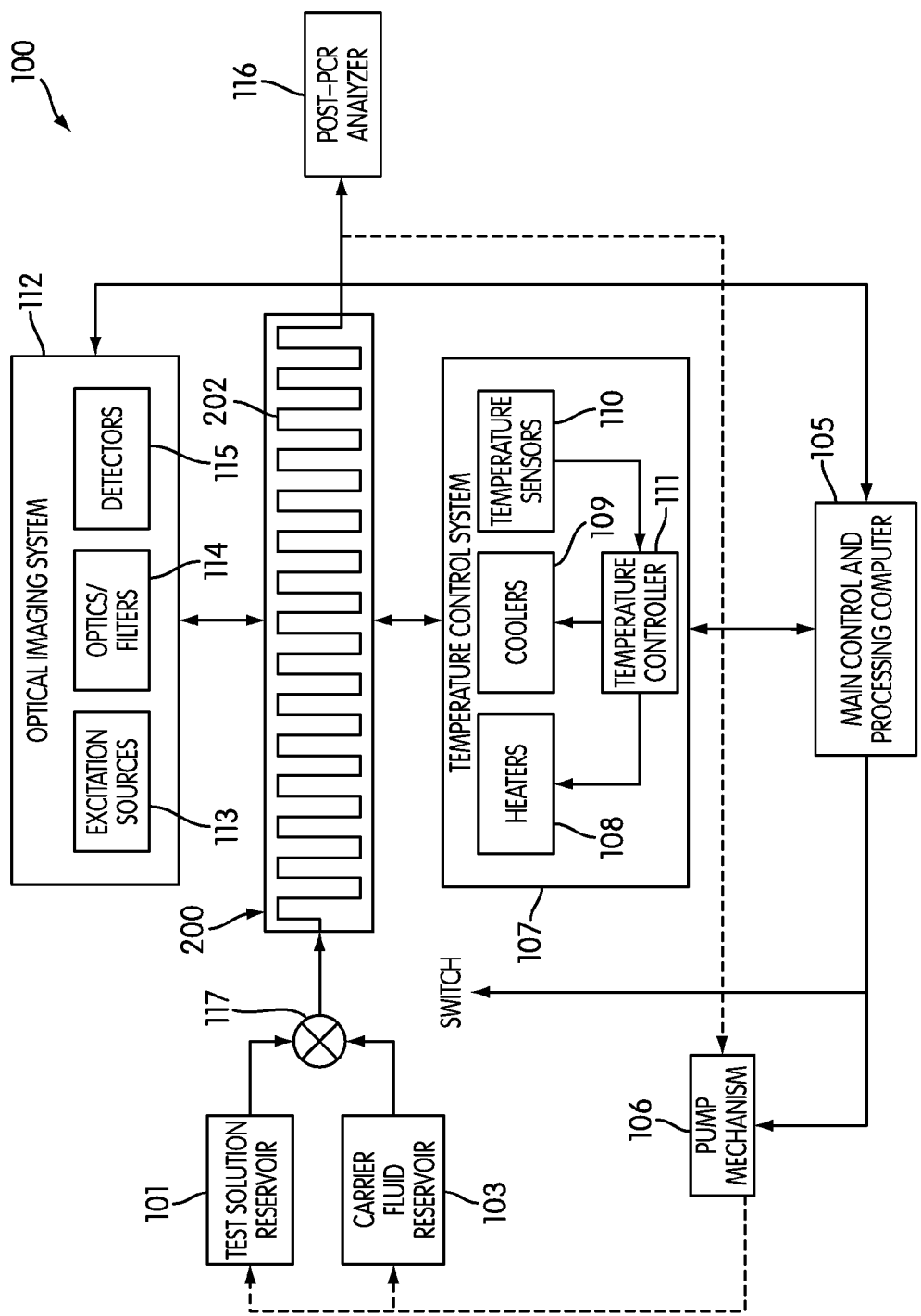
FIG. 1 is a block diagram illustrating a system according to some embodiments of the invention.

FIG. 1 illustrates a block diagram of a system 100 for performing a thermocyclic process, such as real-time PCR, with which the present invention may be implemented. The system 100 may include a source of sample material, such as test solution reservoir 101, which may contain multiple test solutions, e.g., test samples. The system may further include a source of carrier fluid, such as carrier fluid reservoir 103. The solution fluid reservoir 101 and/or the carrier fluid reservoir 103 may comprise chambers within a cartridge that is coupled to the microfluidic device, such as the cartridge described in commonly-assigned U.S. patent application Ser. No. 11/850,229, the disclosure of which is hereby incorporated by reference in its entirety.

The test solution may be substantially the same as the carrier fluid, except that the test solution comprises all the necessary real-time PCR reagents. The real-time PCR reagent mixture may include, for example, PCR primers, dNTPs, polymerase enzymes, salts, buffers, surface-passivating agents, and the like. In addition, the real-time PCR mixture may include a non-specific fluorescent DNA detecting molecule, a sequence-specific fluorescent DNA probe, or a marker. The carrier fluid may be an immiscible fluid (such as an oil, a fluorinated liquid, or any other nonaqueous or hydrophobic solvent). The purpose of the carrier fluid is to deter transfer of material from one test bolus to another. Another purpose of the carrier fluid is to provide a distinguishable transition between boluses that may be used to track the fluid flow in the channel. The carrier fluid may include a marker.

The test solution and carrier fluid are introduced into a microchannel 202 of a microfluidic chip 200, for example, through a switch 104. The dimensions of the microchannel are small enough to allow for the amplification and detection of a single DNA molecule originally present in the test solution. Switch 104 may be under the control of a main control and processing computer 105 such that the carrier fluid and the test solution are sequentially, alternately introduced into microchannel 202. The volume of the test solution and carrier fluid that is introduced into microchannel 202 is selected such that there is minimal blending between them during movement through microchannel 202.

Alternatively, sample material may be provided as a continuous stream in the microchannel 202, and assay-specific reagents and buffer material may be alternately introduced into the continuous stream of sample material, e.g., to create a sequential arrangement of discrete test boluses flowing through the microchannel.

A multitude of reactions in series (or sequential reactions) can thus be carried out in the same microchannel 202 as a result of the continuous movement of different test solutions through microchannel 202, each separated by the carrier fluid. The flow rate of the carrier fluid and test solution through microchannel 202 is controlled by pump mechanism 106. Pump mechanism 106 is under the control of main control and processing computer 105 in order to regulate the flow rate of the test solution and the carrier fluid in microchannel 202.

Pump mechanism 106 can regulate the flow rate of the test solution and carrier fluid by positive pressure at the upstream side or inlet of microchannel 202 or by negative pressure at the downstream side or outlet of microchannel 202. In one embodiment, the pressure difference is approximately 1 psi, although other pressure differences may be utilized.

A temperature control system 107 is included in the system to control the temperature to produce suitable temperatures for the PCR cycles as the test solution moves through microchannel 202. Suitable temperatures for the PCR cycles are well known to skilled artisan and may include a first temperature in the range of about 85° C. to about 100° C., a second temperature in the range of about 20° C. to about 70° C., and a third temperature in the range of about 55° C. to about 80° C. Temperature control system 107 may include thermal elements (i.e., thermal energy sources), such as heaters 108 and/or coolers 109, temperature sensors 110, and a temperature controller 111. Temperature controller 111 collects temperature information from the temperature sensors 110, and generates control signals based on the temperature information. Temperature controller 111 is under control of main control and processing computer 105 so that the desired temperatures are maintained in the heaters 108 and/or coolers 109.

Heating and cooling may be accomplished by circulating water or fluid baths or by Peltier-effect elements which are well known to the skilled artisan.

System 100 may further include an optical imaging system 112, which detects emissions (e.g., fluorescence or chemiluminescence) which are indicative of the presence— and possibly the amount—of a nucleic acid of interest (i.e., amplification products) and to monitor the flow rate of the test solution in microchannel 202. In one embodiment, the optical imaging system 112 is a fluorescent imaging system that preferably includes one or more excitation sources 113, one or more optics/filters modules 114, and one or more detectors 115. The excitation sources 113 generate light at desired wavelengths to excite the labels used for detecting the amplification products during real-time PCR and/or to detect markers that may be present to monitor the flow rate of the test solution in microchannel 202. In addition to filters, optics/filters 114 may include, lenses, light pipes, mirrors, beam splitters, etc. and are used to form a beam of light and/or to direct the light from excitation sources 113 to the appropriate positions on the microchannel 202. Optics/filters 114 are also used to direct a portion of the emission light toward the detectors 115 and to filter the light to exclude light of undesired wavelengths or to reduce backscatter from reaching detectors 115. The desired wavelengths to excite the labels used in real-time PCR will depend on the precise labels and/or markers used, e.g., intercalating dyes, molecular beacons, quantum dots or TaqMan® probes, which wavelengths are well known to skilled artisans. Similarly, the emission wavelengths of the precise labels and/or markers are well known to skilled artisans. Detectors 115 detect the emission wavelengths of the excited labels and/or markers and measure the intensity of the emitted light. Optical imaging system 112 preferably is able to distinguish between multiple microchannels in a microfluidic device.

Optical imaging system 112 is under control of main control and processing computer 105 which directs the optical imaging system 112 to measure the intensity of the emitted light at desired time intervals, such as, for example, at least once during each PCR cycle at one or a plurality of locations in microchannel 202. Detectors 115 generate a signal or an image of the intensity of the emitted light and direct it to main control and processing computer 105 for analysis of the amplification product and for monitoring the flow rate of the test solution. Detectors 115 may include multiple-pixel array detectors (such as a CMOS or CCD detector) and/or discrete single-pixel or non-imaging detectors. Detectors 115 may be integral with or proximal to microchannel 202 or to the microchannels of a microfluidic device. Detectors 115 may be stationary or may be scanning. The detectors 115 should have appropriate resolution for obtaining meaningful results and for monitoring of fluid flow in microchannel 202, particularly because the fluid is continuously moving in microchannel 202.

The real-time PCR mixture may include a non-specific fluorescent DNA detecting molecule (such as an intercalating dye), a sequence-specific fluorescent DNA probe (such as a molecular beacon, a TaqMan® probe, or a quantum dot probe), or a flow marker (such as a quantum dot), and the carrier fluid may include a flow marker. In one embodiment, the optical imaging system 112 is utilized to detect the intensity of the fluorescence from the DNA detecting molecule or the probe (i.e., the intensity of the fluorescent signal) and/or to detect the fluorescence of the marker. The fluorescence of the marker can be used to delineate the test solution from the carrier fluid and can also be used to determine and monitor the flow speed of the test solution or carrier fluid. The intensity of the fluorescent signal can be used to detect amplified product, to determine the quantity of amplified product, to determine the number of original molecules present in the test solution, and the like as well known to a skilled artisan for real-time PCR. The intensity of the fluorescent signal can also be used to determine and monitor the flow speed of the test solution.

The intensity of the fluorescent signal may be measured (e.g., an image of the fluorescent signal is taken) at a specific time and/or temperature during the PCR temperature cycle. Alternatively, the intensity of the fluorescent signal can be measured once during each PCR cycle.

After test solution has moved through microchannel 202 and completed the desired number of PCR cycles, it may optionally be sent to a post-PCR analyzer 116. Post-PCR analyzer 116 may include any analytical technique that can be used on PCR amplification products. Such techniques include, but are not limited to, sequencing, electrophoresis, probing, thermal melt curve analysis, and the like.

Figure 2:
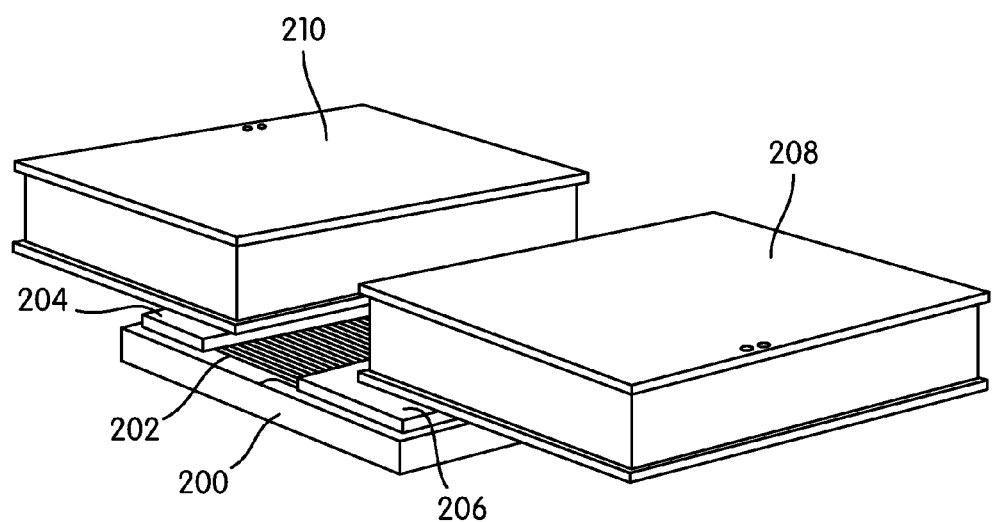
FIG. 2 is a perspective view of an exemplary arrangement of heaters and a microfluidic chip with thermal distribution elements embodying aspects of the present invention.

Aspects of the present invention are embodied in an arrangement including thermal elements 208 and 210 in combination with a microfluidic chip 200 having thermal distribution elements 204, 206 as shown in FIG. 2. The microfluidic chip 200 may be fabricated in any suitable size, preferably in the range of 1 $cm^2$ to 100 $cm^2$, and most preferably approximately 20 mm×20 mm, and is ideally manufactured from any suitable material, including borosilicate glass, quartz glass, plastic polymers, and silicon. One or more microfluidic channels, or microchannels, 202 are formed on the surface of the chip 200 for moving sample solution therethrough. The microfluidic channel 202 is preferably arranged in a serpentine manner extending transversely across the surface of the chip 200 substantially from one side of the chip to the other and back.

The microfluidic channel 200 traverses through the chip from an inlet side to an outlet side and is moved via typical and known means of pressure-driven flow. Flow rates may vary between about 10 nanoliters per minute to about 1 milliliter per minute. The serpentine pattern of the microchannel is repeated numerous times to provide sample exposure to PCR temperature cycles. In one embodiment, the number of across and back serpentine patterns is approximately 40, but can be in the range of 20 to 60. A preferred embodiment includes 30 to 50 serpentine patterns and most preferably includes 30 to 40 serpentine patterns.

Thermal distribution elements 204 and 206 are secured to the chip 200 overlying portions of the microfluidic channel 202. In the embodiment shown in FIG. 2, the thermal distribution elements 204 and 206 are elongated plates formed from a thermally conductive material, preferably a metal, most preferably copper (less preferably aluminum), and are positioned on the chip 200 so as to extend substantially from one end of the chip to the opposite end of the chip. The thermal distribution elements 204 and 206 are preferably secured to the microfluidic chip 200 by a thermally conductive adhesive, such as a thermally conductive epoxy.

The heating elements 208 and 210 may comprise elements of the heaters 108 and/or coolers 109 of the temperature control system 107 (see FIG. 1). The heaters, or thermal generating devices, are capable of applying heat or cold to the microfluidic chip. Heaters 208 and 210 may comprise any type of heating device including resistive, thermal electric, Peltier, etc. The temperatures of the heaters 208 and 210 are precisely controlled at fixed temperatures and have a thermal mass greater than that of the chip 200. Temperature control is maintained by the temperature sensors 110 of the temperature control system 107 (see FIG. 1), which may include any suitable type of temperature measuring devices, such as thin film resistors, thermistors, or thermocouples.

Figure 3:
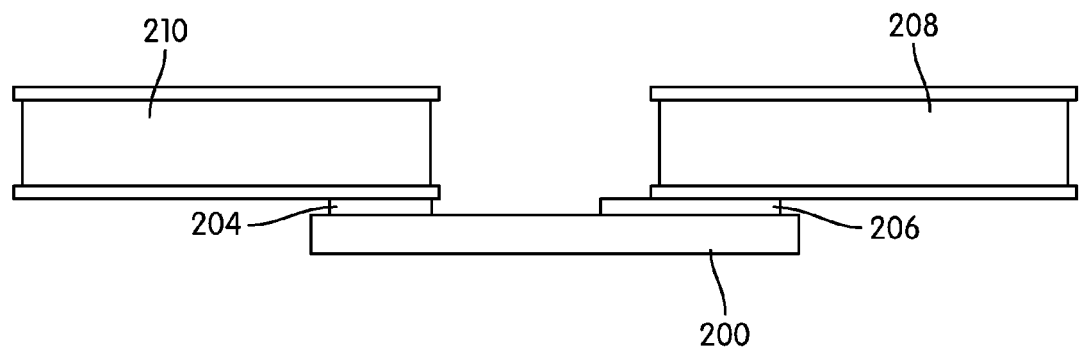
FIG. 3 is a side view of the arrangement shown in FIG. 2.

As shown in FIGS. 2 and 3, heaters 208 and 210 are placed in contact with the thermal distribution elements 204 and 206, for example, by placing the microfluidic chip 200 into the system 100 shown in FIG. 1. Thermal energy generated by the heaters 208 and 210 is transferred, via the thermal distribution elements 204 and 206, respectively, to the microfluidic chip 200. The thermal distribution elements 204 and 206 function to not only transfer thermal energy from the heaters 208 and 210 to the microfluidic chip 200, but also to provide a substantially uniform distribution of the transferred thermal energy across a discrete area defined by the portion of the thermal distribution element in contact with the chip. The microfluidic chip 200 is preferably made from a material that is a poor thermal conductor, and thus, the thermal energy transferred to the microfluidic chip 200 via the thermal distribution elements 204 and 206 is substantially confined to the area of the thermal distribution element that is in contact with the microfluidic chip 200.

Figure 4:
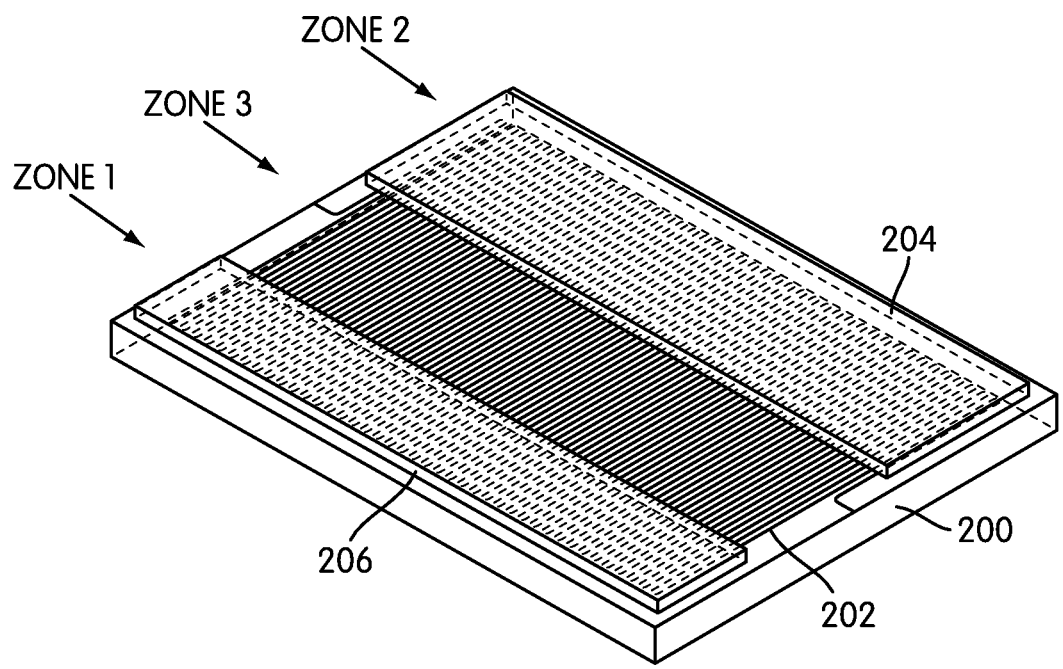
FIG. 4 is a perspective view of the microfluidic chip of FIG. 2 and illustrates three temperature zones that are defined by the arrangement shown in FIGS. 2 and 3.

Accordingly, it can be appreciated that the arrangement illustrated in FIGS. 2 and 3 creates three distinct temperature zones. This is illustrated in FIG. 4. A first zone ("zone 1") corresponds to that portion of the microfluidic chip 200 covered by the thermal distribution element 206. A second zone ("zone 2") corresponds to that portion of the microfluidic chip 200 that is covered by the thermal distribution element 204. Finally, a third zone ("zone 3") is defined by that portion of the microfluidic chip 200 that is between the portions covered by thermal distribution elements 204 and 206 and is not in contact with a thermal distribution element. It can be further appreciated that as material flows through the serpentine path of the microchannel 202, the fluid will sequentially pass through zones 1, 3 and 2 a number of times as the fluid traverses the length of the microchannel 202.

The temperature of the third zone may be controlled by other means including flowing air of a controlled temperature passing over the microfluidic chip 200.

To effect PCR on sample fluid flowing through the microfluidic channel 202, heater device 210 would typically be adjusted to approximately 94° C. to achieve the denaturation temperature of the PCR in zone 1. Heater device 208 would typically be adjusted to approximately 50° C. to achieve the annealing temperature of the PCR in zone 3. Accordingly, fluid sample flowing through the microchannel 202 will pass through the zones 1, 2 and 3, and thus will be exposed to the discrete temperatures of each of those zones thereby effecting rapid temperature transitions to achieve the necessary thermal cycling to accomplish PCR.

Figure 5:
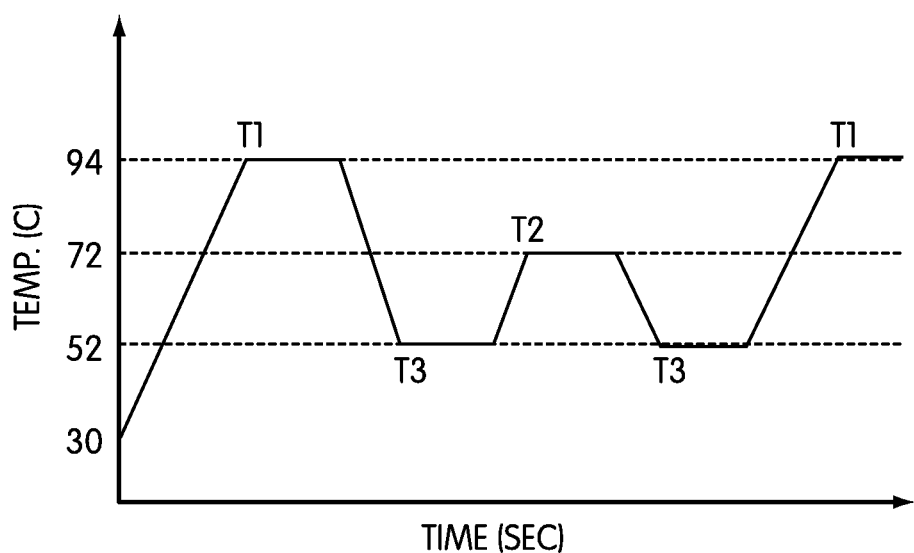
FIG. 5 is an exemplary temperature profile showing temperature cycling that can be achieved in accordance with aspects of the present invention.

FIG. 5 shows a typical temperature profile showing the temperature transition that can be accomplished with an arrangement such as that shown in FIGS. 2, 3 and 4. In the illustrated profile, the sample material is exposed to the temperature of zone 1 (T1) for a period of time required to traverse across and back zone 1. From zone 1, the sample flows into zone 3 and is exposed to the temperature of zone 3 (T3) for a period of time required to cross zone 3. From zone 3, the sample flows into zone 2 and is exposed to the temperature of zone 2 (T2) for a period of time required to traverse across and back zone 2. From zone 2, the sample flows back into zone 3 where it is exposed to temperature T3. The period of exposure at each temperature will depend on the length of microchannel within the corresponding temperature zone and the sample flow rate.

Examples of thermal distribution element location and size variations are shown in FIGS. 6A through 6D. As sample materials move linearly through the serpentine microchannels, the sample traverses the changing temperature-controlled regions. The length of time within a given temperature zone, dwell time, is controlled by the width (top to bottom in FIGS. 6A through 6D) of the thermal distribution element defining that zone.

Figure 6A:
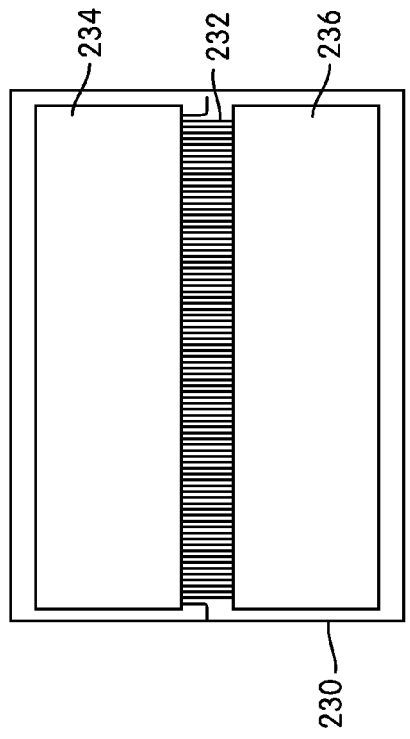
FIGS. 6A-6D are plan views of microfluidic chips illustrating other exemplary arrangements of thermal distribution elements.

FIG. 6A shows a microfluidic chip 220 having a serpentine microchannel 222 and relatively small thermal distribution elements 224 and 226 that are approximately of the same size. Accordingly, the temperature regions defined by thermal distribution elements 224 and 226 are relatively small as compared to the temperature region defined between the thermal distribution elements. Thus, the dwell times at the temperatures corresponding to the zones defined by thermal distribution elements 224 and 226 is less than that in the temperature zone defined between the thermal distribution elements.

Figure 6B:
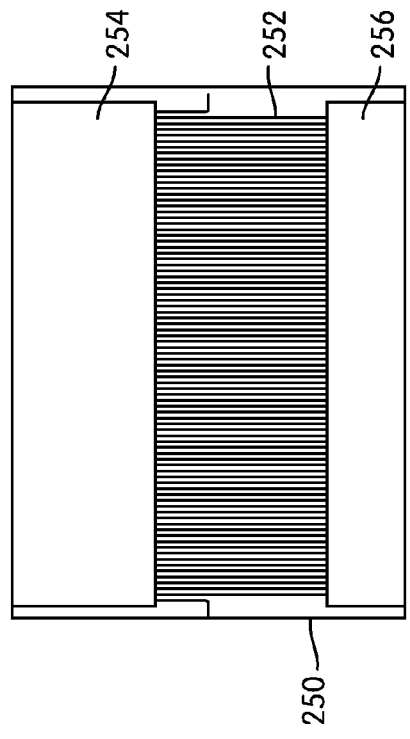

In FIG. 6B, microfluidic chip 230 includes a serpentine microchannel 232 and thermal distribution elements 234 and 236 which are approximately the same size and are relatively wide as compared to the temperature region defined between the thermal distribution elements. Accordingly, the dwell times in the temperature zones defined by thermal distribution elements 234 and 236 would be greater than the dwell time within the temperature zone defined between the thermal distribution elements.

Figure 6C:
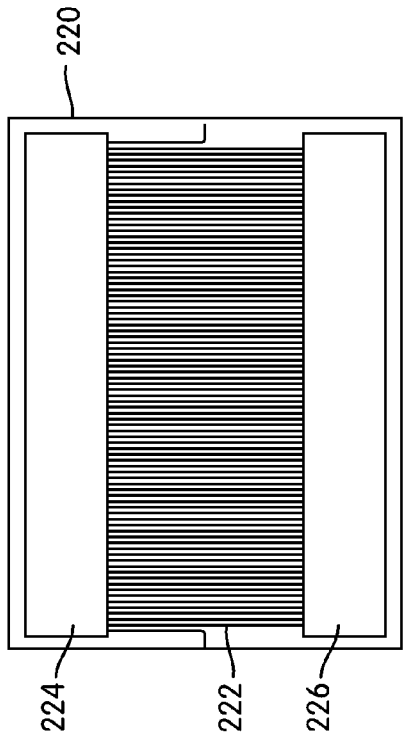

In FIG. 6C, microfluidic chip 240 includes a serpentine microchannel 242 and thermal distribution elements 244 and 246. Thermal distribution element 246 is larger than thermal distribution element 244. Accordingly, dwell time within the temperature zone defined by the thermal distribution element 246 would be greater than the dwell time within the temperature zone defined by thermal distribution element 244.

Figure 6D:
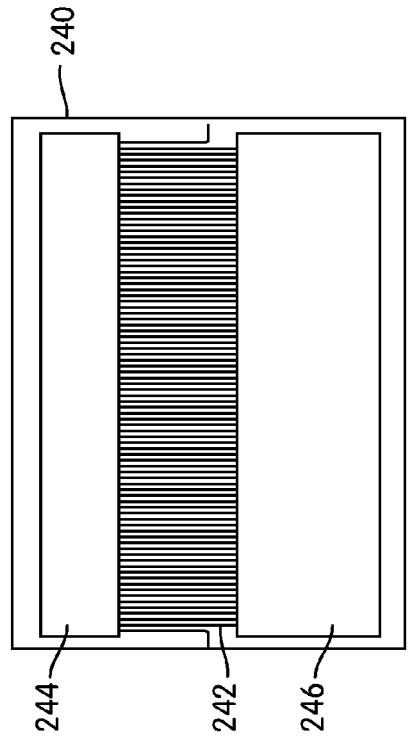

In FIG. 6D, microfluidic chip 250 includes a serpentine microchannel 252 and thermal distribution elements 254 and 256. Thermal distribution element 254 is larger than the thermal distribution element 256. Accordingly, the dwell time within the temperature zone defined by thermal distribution element 254 would be greater than a dwell time within the temperature zone defined by thermal distribution element 256.

As can be appreciated by persons of ordinary skill in the art, many dwell time profiles can be derived by changing the size and shape of the thermal distribution elements. By adjusting the width of the thermal distribution element (where the microchannel is oriented so that sample flowing through the microchannel traverses across the width of the thermal distribution element), the size of the temperature zone is proportionally adjusted. The effect is a change in the dwell time of the PCR cycle due to the fact that the sample drop will move through the microchannel at a substantially constant velocity. This would permit adjustment to a particular, optimized assay. And thus, different assay chips could then be fabricated with different dwell time profiles by controlling the size and shape of the thermal distribution elements as well as the orientation of the microchannel(s) relative to the thermal distribution element.

Figure 7:
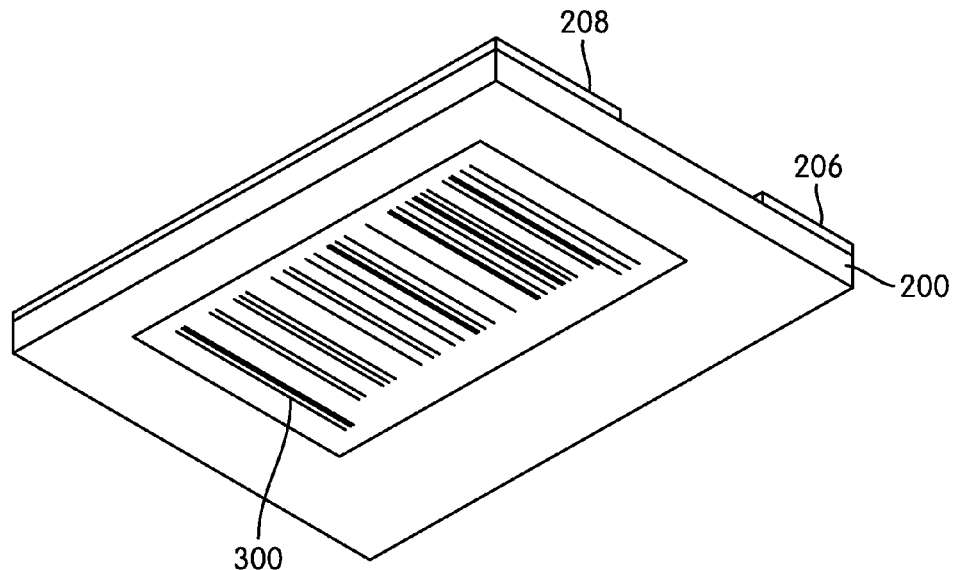
FIG. 7 is a bottom perspective view of a microfluidic chip showing a machine-readable bar code on the bottom of the chip.

An advantage of the instant invention is that microfluidic chips can be prepackaged for optimized assay designs, e.g. specific diagnostic/analytical tests, that optimize the PCR reaction. As shown in FIG. 7, during chip fabrication, a label 300 can be affixed to the chip so that the instrument can readily identify the chip via an optical detector reading the label. Preferably, the labeling is machine readable, for example, a bar code or RFID tag. The instrument will then adjust the assay and instrument process control to that of the specific PCR protocol mandated by the inserted chip. The microfluidic chips are preferably disposable.

The arrangement described herein utilizes a purposeful open center section, previously described as zone 3. This section preferably defines the temperature region wherein the PCR amplification extension phase occurs. The section is optically clear to allow fluorescence excitation and detection apparatus to probe and measure the microchannel area continuously without interference from the heating mechanisms or the thermal distribution elements. Zone 3 is typically temperature-controlled to approximately 74° C., for example, by flowing air at the same temperature over zone 3.

Other embodiments of the invention permit zone 3 to consist of alternating temperatures to attain a true three-step PCR reaction. In still further embodiments, a two-step PCR reaction is possible by minimizing the size of zone 3 such that the sample passes immediately from zone 1 to zone 2.

Figure 8:
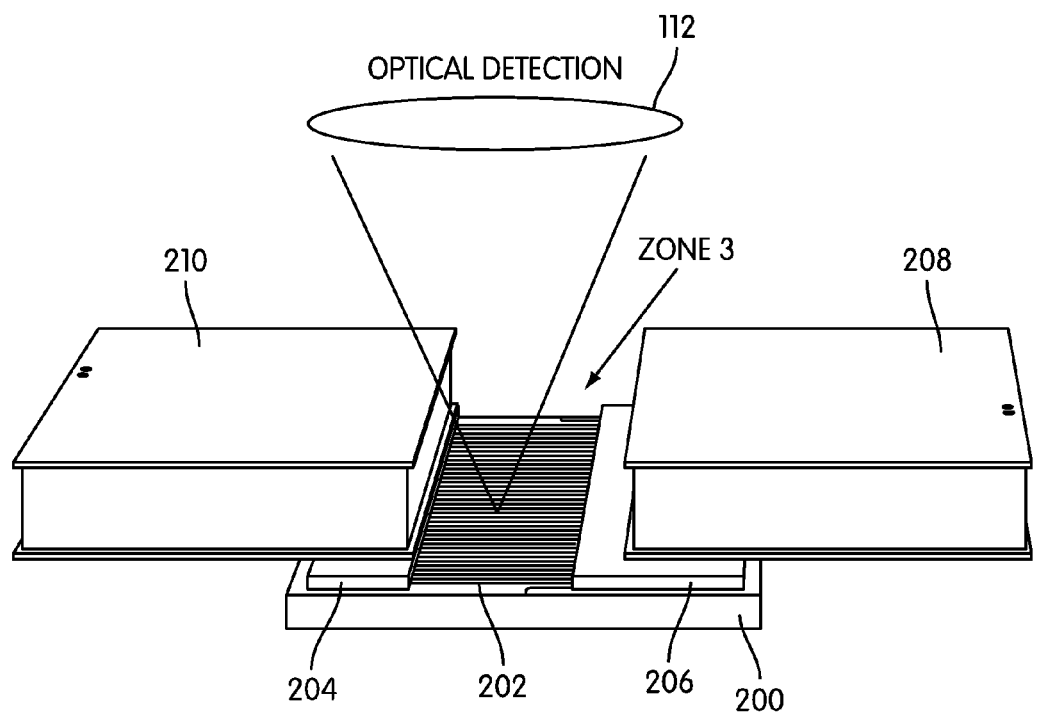
FIG. 8 is a perspective view of heaters and a microfluidic chip with thermal distribution elements illustrating that at least a portion of a defined temperature zone may be within the field of view of a detector.

Real-time PCR measurements are typically performed at the end of the extension phase of the PCR cycle. The microfluidic chip described herein facilitates this by design. As shown in FIG. 8, the optical imaging system 112 can be positioned and configured so as to be directed at zone 3, which is unobstructed by heating elements 208, 210 or thermal distribution elements 204, 206.

Figure 9A:
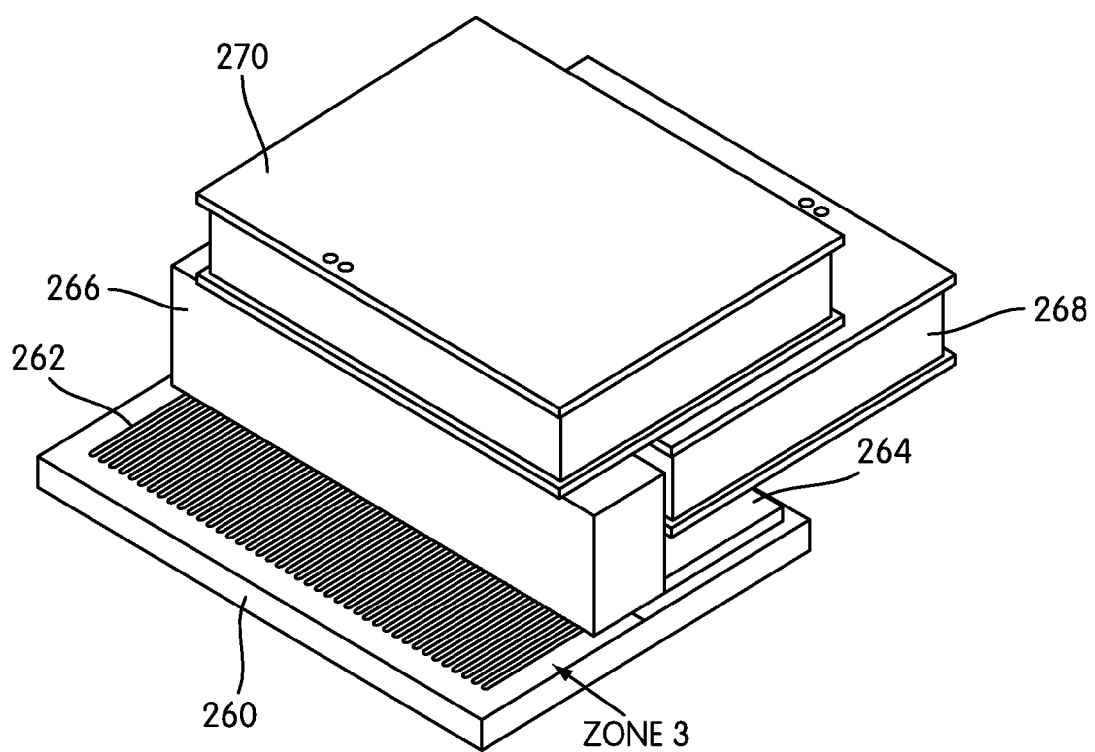
FIG. 9A is a perspective view of an alternative arrangement of heaters and a microfluidic chip with thermal distribution elements embodying aspects of the present invention.
Figure 9B:
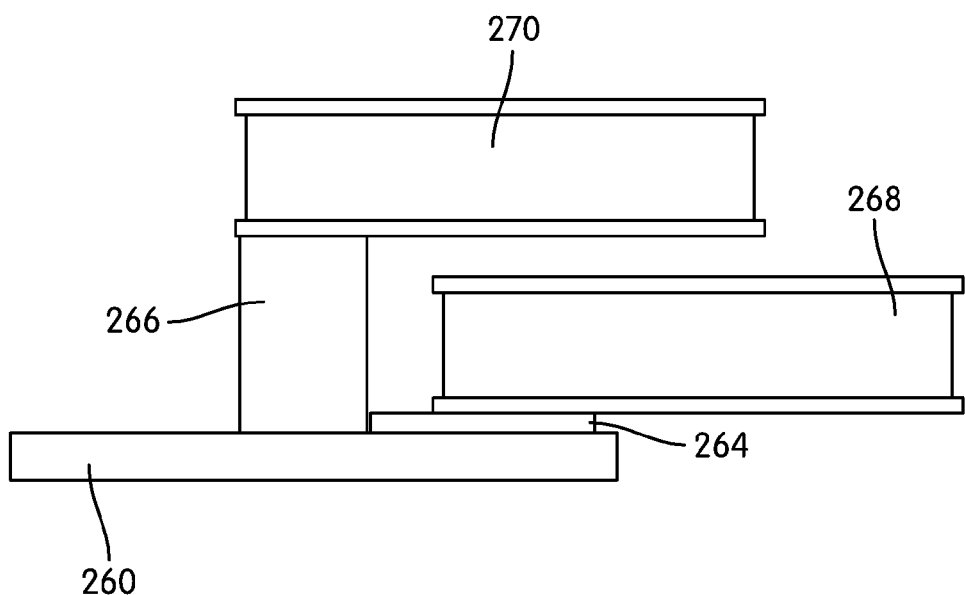
FIG. 9B is a side view of the arrangement shown in FIG. 9A.

FIGS. 9A and 9B illustrate an arrangement whereby zone 3 (i.e., the zone without a thermal distribution element) is positioned at a location other than the center of the chip, for example along one edge of the chip as shown. In the arrangement shown, microfluidic chip 260 includes a microchannel 262 and thermal distribution elements 264 and 266. Thermal distribution element 264 is a generally plate-like panel disposed over portion of the chip so as to cover a portion of the microchannel 262. Thermal distribution element 266 is in the form of an elongated rectangular block having a length substantially the same as that of thermal distribution element 264, but a thickness substantially greater than that of thermal distribution element 264. Heating element 268 is placed in contact with thermal distribution element 264. Furthermore, heating element 270 is placed in contact with thermal distribution element 266, and because thermal distribution element 266 is thicker than heating element 268, heating element 270 can be placed above heating element 268 without contacting heating element 268.

Figure 10A:
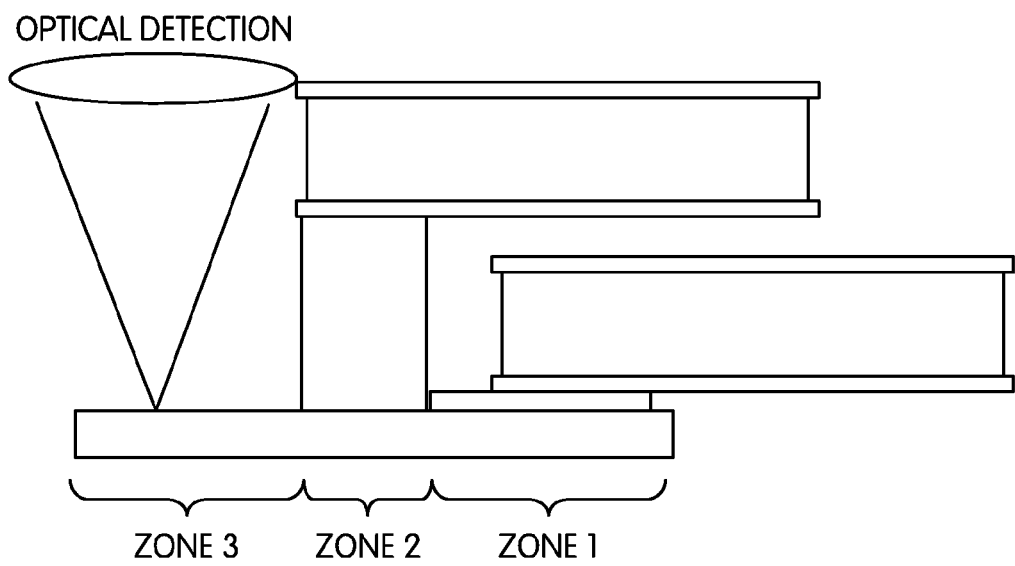
FIGS. 10A-10B illustrate various possible arrangements of a detector in combination with the arrangement of FIGS. 9A and 9B.
Figure 10B:
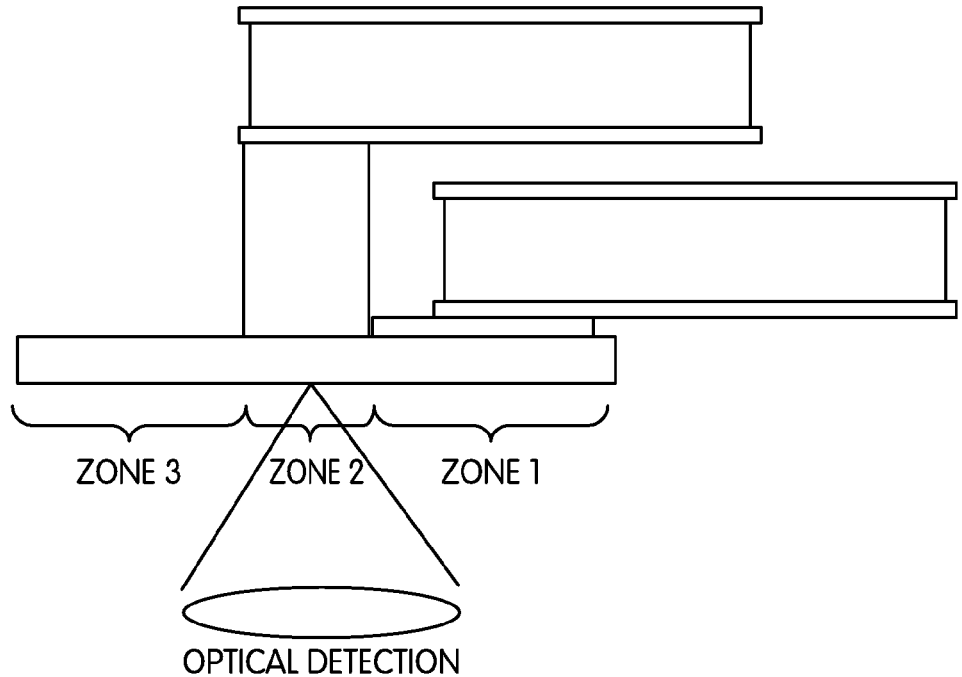

FIGS. 10A and 10B show the arrangement illustrated in FIGS. 9A and 9B and identify the temperature zones defined by the thermal distribution elements 264 and 266 and the portion of the microfluidic chip 260 that is uncovered by a thermal distribution element. FIGS. 10A and 10B also illustrate possible positions for an optical detection system with respect to the microfluidic chip. As shown, the optic devices for measuring real time PCR fluorescence can be physically located above or below the chip. Furthermore, as shown in FIG. 10B, the location of the optic device below the chip for the purpose of measuring the fluorescence can be at any PCR zone location, for example zone 2, as shown, which is below thermal distribution element 266 and heater 270.

Figure 11:
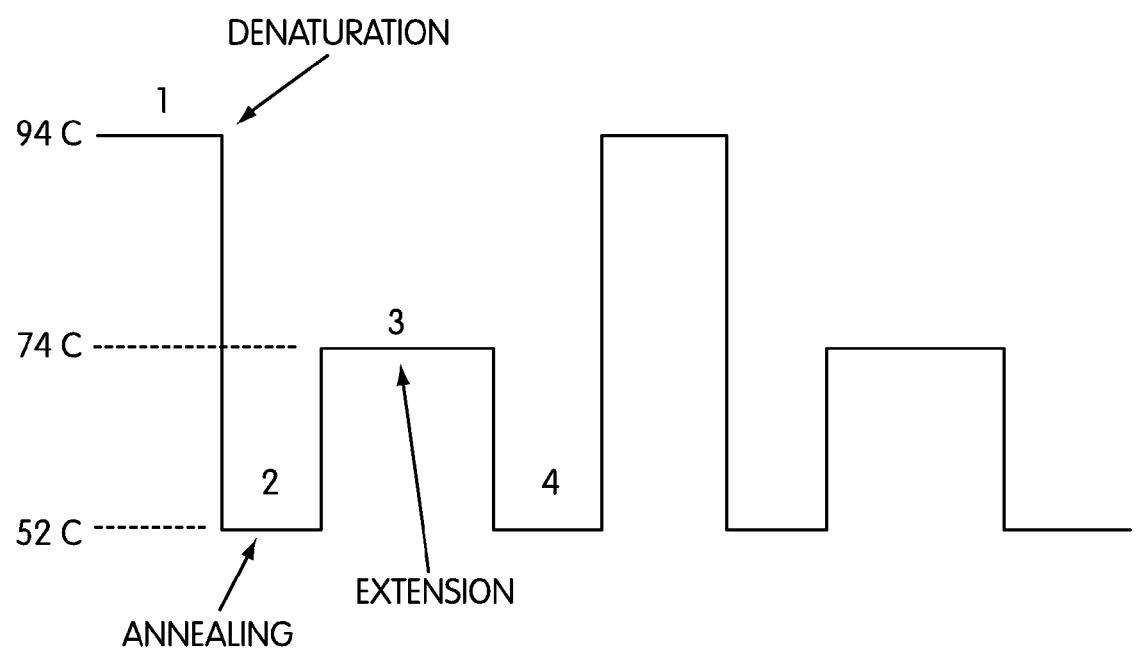
FIG. 11 illustrates an exemplary temperature profile.

A further embodiment of the invention details a four-step PCR process. If the area of zone 3 of the arrangement shown in FIGS. 2 and 3 is simply adjusted to the extension temperature, e.g., approximately 74° C., then a four-step PCR process would be generated. A temperature profile for such an arrangement is shown in FIG. 11.

While various embodiments/variations of the present invention have been described above, it should be understood that they have been presented by way of example only, and not limitation. Thus, the breadth and scope of the present invention should not be limited by any of the above-described exemplary embodiments. Further, unless stated, none of the above embodiments are mutually exclusive. Thus, the present invention may include any combinations and/or integrations of the features of the various embodiments.

Additionally, while the processes described above and illustrated in the drawings are shown as a sequence of steps, this was done solely for the sake of illustration. Accordingly, it is contemplated that some steps may be added, some steps may be omitted, and the order of the steps may be rearranged.

What is claimed is:

1. An adaptable apparatus for performing a thermocyclic process comprising:
   a microfluidic chip having a fluid channel formed therein; and
   one or more thermal distribution elements, each of which is separate from the microfluidic chip;
   wherein the one or more thermal distribution elements are placed in thermal communication with an associated portion of said microfluidic chip, each said thermal distribution element being constructed and arranged to distribute thermal energy from an external thermal energy source, including at least one heater, substantially uniformly over said associated portion of said microfluidic chip, wherein each of the one or more thermal distribution elements is positioned between and in contact with the microfluidic chip and the at least one heater,
   wherein the size and positioning of the one or more heaters and thermal distribution elements in relation to the fluid channel creates two or more adaptable temperature zones on the microfluidic chip, thereby defining said associated portion as one of said temperature zones within said microfluidic chip,
   a detector configured to detect emissions originating from one or more locations within the channel, wherein the one or more heaters and thermal distribution elements positioned on the same side as the detector relative to the microfluidic chip obstruct optical communication between the detector and a fluid in the fluid channel passing through temperature zones in thermal communication with the thermal distribution elements, wherein fluid passing through a temperature zone not in thermal communication with the thermal distribution element is in optical communication with the detector,
   wherein the size and positioning of the one or more thermal distribution elements in relation to the microfluidic chip is changeable,
   wherein said channel is arranged such that the fluid flowing through the channel would enter and exit each of said temperature zones of the microfluidic chip a plurality of times.

2. The apparatus of claim 1, wherein one of said temperature zones comprises a portion of said fluid channel that is not in thermal communication with any of said thermal distribution elements, wherein said detector is configured to detect emissions originating from locations within substantially only the temperature zone not in thermal communication with any of said thermal distribution elements.

3. The apparatus of claim 1, comprising:
   a first temperature zone defined by a first thermal distribution element;
   a second temperature zone defined by a second thermal distribution element; and
   a third temperature zone comprising a portion of said fluid channel that is not in thermal communication with any of said thermal distribution elements, wherein said detector is configured to detect emissions originating from locations within substantially only said third temperature zone.

4. The apparatus of claim 1, wherein each said thermal distribution element comprises a thermally conductive material adhered to the associated portion of the microfluidic chip.

5. The apparatus of claim 4, wherein said thermal distribution element comprises a metal plate.

6. The apparatus of claim 4, wherein said thermal distribution element comprises a rectangular metal block.

7. The apparatus of claim 1, wherein said channel is configured in a serpentine pattern.

8. The apparatus of claim 1, further comprising a label including information which can be used to identify characteristics of the thermocyclic process that can be performed with the apparatus based on characteristics of said temperature zones of said microfluidic chip.

9. The apparatus of claim 8, wherein characteristics of said temperature zones which determine characteristics of the thermocyclic process that can be performed with the apparatus include the number and sizes of said temperature zones as determined by the sizes of said thermal distribution elements.

10. The apparatus of claim 8, wherein said label comprises a machine-readable label.

11. The apparatus of claim 10, wherein said label comprises a bar code.

12. The apparatus of claim 10, wherein said label comprises an RFID tag.

13. The apparatus of claim 1, wherein altering the size and/or position of the thermal distribution elements changes the amount of time a fluid flowing through the microfluidic channel will spend in each temperature zone.

14. An adaptable system for performing a thermocyclic process, said system comprising:
a microfluidic chip having a fluid channel formed therein; and
one or more thermal distribution elements, each of which is separate from the microfluidic chip;
wherein the one or more thermal distribution elements are placed in thermal communication with an associated portion of said microfluidic chip, each said thermal distribution element being constructed and arranged to distribute thermal energy from an external thermal energy source, including a heater, substantially uniformly over said associated portion of said microfluidic chip, wherein each of the one or more thermal distribution elements is positioned between and in contact with the microfluidic chip and the heater,
wherein the size and positioning of the one or more thermal distribution elements in relation to the fluid channel creates two or more adaptable temperature zones on the microfluidic chip, thereby defining said associated portion as one of said temperature zones within said microfluidic chip,
wherein the size and positioning of the one or more thermal distribution elements in relation to the microfluidic chip is changeable,
wherein said channel is arranged such that the fluid flowing through the channel would enter and exit each of said temperature zones of the microfluidic chip a plurality of times;
a detector configured to detect emissions originating from one or more locations within the channel, wherein the one or more heaters and thermal distribution elements positioned on the same side as the detector relative to the microfluidic chip obstruct optical communication between the detector and a fluid in the fluid channel passing through temperature zones in thermal communication with the thermal distribution elements, wherein a fluid passing through temperature zones not in thermal communication with the thermal distribution elements is in optical communication with the detector.

15. The system of claim 14, wherein said heater comprises a Peltier heater.

16. The system of claim 15, wherein said heater comprises a circulating fluid heater.

17. The system of claim 14, wherein said thermal energy source comprises a cooler.

18. The system of claim 14, wherein the thermal mass of each thermal energy source is greater than the thermal mass of said microfluidic chip.

19. The system of claim 14, further comprising:
an excitation source; and
optics elements for directing at least a portion of the excitation light toward the channel and for directing at least a portion of the emission light from the channel toward said detector.

20. The system of claim 14, further comprising:
a reservoir storing a solution containing a nucleic acid sample; and
a pump configured to pump the solution out of the reservoir and into the channel such that the solution will travel through the channel at a substantially constant speed.

21. The system of claim 14, wherein one of said temperature zones comprises a portion of said fluid channel that is not in thermal communication with any of said thermal distribution elements, wherein said detector is configured to detect emissions originating from locations within substantially only the temperature zone not in thermal communication with any of said thermal distribution elements.

22. The system of claim 14, comprising:
a first temperature zone defined by a first thermal distribution element;
a second temperature zone defined by a second thermal distribution element; and
a third temperature zone comprising a portion of said fluid channel that is not in thermal communication with any of said thermal distribution elements.

23. The system of claim 22, wherein said detector is configured to detect emissions originating from locations within substantially only said third temperature zone.

24. The system of claim 14, wherein each said thermal distribution element comprises a thermally conductive material adhered to the associated portion of the microfluidic chip.

25. The system of claim 24, wherein said thermal distribution element comprises a metal plate.

26. The system of claim 14, wherein said channel is configured in a serpentine pattern.

27. The system of claim 14, wherein said microfluidic chip further comprises a label including information which can be used to identify characteristics of the thermocyclic process that can be performed with the microfluidic chip based on characteristics of said temperature zones of said microfluidic chip.

28. The system of claim 27, further comprising a computer controller configured to control operation of said thermal energy source and said detector based at least in part on information included on said label.

29. The system of claim 28, further comprising a pump configured to pump fluid into the channel and wherein said controller is further configured to control operation of said pump based at least in part on information included on said label.

30. The system of claim 14, further comprising a computer controller configured to control operation of said thermal energy source and said detector.

31. The system of claim 14, wherein altering the size and/or position of the thermal distribution elements changes the amount of time a fluid flowing through the microfluidic channel will spend in each temperature zone.

32. An adaptable apparatus for performing a thermocyclic process comprising:
 a microfluidic chip comprising a first material and having a fluid channel formed therein; and
 one or more thermal distribution elements comprising a second material; wherein the one or more thermal distribution elements are placed in thermal communication with an associated portion of said microfluidic chip, each said thermal distribution element being constructed and arranged to distribute thermal energy from an external thermal energy source, including a heater, substantially uniformly over said associated portion of said microfluidic chip, wherein each of the one or more thermal distribution elements is positioned between and in contact with the microfluidic chip and the heater,
 wherein the size and positioning of the one or more heaters and thermal distribution elements in relation to the fluid channel creates two or more adaptable temperature zones on the microfluidic chip, thereby defining said associated portion as one of said temperature zones within said microfluidic chip,
 a detector configured to detect emissions originating from one or more locations within the channel, wherein the one or more heaters and thermal distribution elements positioned on the same side as the detector relative to the microfluidic chip obstruct optical communication between the detector and a fluid in the fluid channel passing through temperature zones in thermal communication with the thermal distribution elements, wherein a fluid passing through temperature zones not in thermal communication with the thermal distribution elements is in optical communication with the detector,
 wherein the size and positioning of the one or more heaters and thermal distribution elements in relation to the microfluidic chip is changeable,
 wherein said channel is arranged such that the fluid flowing through the channel would enter and exit each of said temperature zones of the microfluidic chip a plurality of times.

* * * * *